(12) United States Patent
Ulrich et al.

(10) Patent No.: US 6,648,930 B2
(45) Date of Patent: Nov. 18, 2003

(54) PRODUCTS COMPRISING CORN OIL AND CORN MEAL OBTAINED FROM HIGH OIL CORN

(75) Inventors: James F. Ulrich, Lake Forest, IL (US); Neal T. Jakel, Lake Zurich, IL (US)

(73) Assignees: Renessen LLC, Bannockburn, IL (US); Cargill, Inc., Wayzata, MN (US)

( * ) Notice: Subject to any disclaimer, the term of this patent is extended or adjusted under 35 U.S.C. 154(b) by 0 days.

(21) Appl. No.: 09/927,836

(22) Filed: Aug. 10, 2001

(65) Prior Publication Data

US 2002/0193617 A1 Dec. 19, 2002

Related U.S. Application Data

(63) Continuation-in-part of application No. 09/637,843, filed on Aug. 10, 2000, which is a continuation-in-part of application No. 09/249,280, filed on Feb. 11, 1999, now Pat. No. 6,313,328.

(51) Int. Cl.$^7$ .................................................. C10L 1/18
(52) U.S. Cl. ............................................................. 44/308
(58) Field of Search ............................................. 44/308

(56) References Cited

U.S. PATENT DOCUMENTS

| | | |
|---|---|---|
| 3,432,529 A | 3/1969 | Demper |
| 3,519,431 A | 7/1970 | Wayne |
| 3,786,078 A | 1/1974 | Finley et al. |
| 3,909,288 A | 9/1975 | Powell et al. |
| 3,939,281 A | 2/1976 | Schwengers |
| 4,008,210 A | 2/1977 | Steele et al. |
| 4,246,184 A | 1/1981 | Pressick et al. |
| 4,277,411 A | 7/1981 | Yahl |
| 4,310,468 A | 1/1982 | Reiners |
| 4,341,713 A | 7/1982 | Stolp et al. |
| 4,442,034 A | 4/1984 | Suzuki et al. |
| 4,456,556 A | 6/1984 | Grimsby |
| 4,456,557 A | 6/1984 | Grimsby |
| 4,486,353 A | 12/1984 | Matsuzaki et al. |
| 4,495,207 A | 1/1985 | Christianson et al. |
| 4,594,260 A | 6/1986 | Vaqueiro et al. |
| 5,035,910 A | 7/1991 | Jones et al. |
| 5,085,808 A | 2/1992 | Snyder et al. |
| 5,320,669 A | 6/1994 | Lim et al. |
| 5,408,924 A | 4/1995 | Arendt et al. |
| 5,525,746 A | 6/1996 | Franke |
| 5,670,678 A | 9/1997 | Rothbart |
| 5,675,065 A | 10/1997 | Bergquist |
| 5,706,603 A | 1/1998 | Bergquist et al. |
| 5,750,851 A | 5/1998 | Geadelmann et al. |
| 5,851,572 A | 12/1998 | Cook et al. |
| 5,908,940 A | 6/1999 | Lane et al. |

FOREIGN PATENT DOCUMENTS

| | | |
|---|---|---|
| EP | 0623100 B1 | 4/1997 |
| GB | 2269084 A | 2/1994 |
| GB | 2309150 A | 7/1997 |
| JP | 6032358 | 2/1994 |
| WO | WO 94/15483 A1 | 7/1994 |
| WO | WO 95/22598 A2 | 8/1995 |
| WO | WO 98/43473 A1 | 10/1998 |
| WO | WO 99/52376 A1 | 10/1999 |
| WO | WO 00/47702 A1 | 8/2000 |
| WO | WO 01/55283 A1 | 8/2001 |
| WO | WO 02/13624 A1 | 2/2002 |
| WO | WO 02/14459 A2 | 2/2002 |

OTHER PUBLICATIONS

Aguilera et al., "Laboratory and Pilot Solvent Extraction of Extruded High–Oil Corn," *JAOCS*1986, 63(2): pp. 239–243, Texas A&M University, College Station, Texas, USA.

Bockisch, Michael, "Fats and Oils Handbook," 1993, pp. 344–391, Hamburg, Germany.

Midwest Research Institute For The Office Of Air Quality And Planning And Standards, Emission Factor Documentation for AP–42, Section 9.11.1, Vegetable Processing, Final Report, Nov. 1995, p. 2–12, Research Triangle Park, North Carolina, USA.

watson, "Corn and Corn Improvement," *Marketing, Processing and Utilization*, 3$^{rd}$ Edition, 1988, No. 18 series Agronomy, pp. 917–918, Madison, Wisconsin, USA.

Watson et al., "Structure and Composition" *Corn: Corn Chemistry and Technology*, 1987, pp. 538–539, St. Paul, Minnesota, USA.

Blessin, "Carotenoids of Corn and Sorghum," *Cereal Chem.*, 59:236–242 (1962).

Blessin et al., "Carotenoids of Corn and Sorghum," *Cereal Chem.*, 40:582–586 (1963).

Grams et al., "Distribution of Tocopherols Within The Corn Kernel," *J. Amer. Oil Chemists Soc.*, 47:337–339 (1970).

Lambert, "High–Oil Corn Hybrids," *Specialty Corns*, pp. 123–145 (1994).

Paulis et al., "Selection of High–Lysine Corns with Varied Kernel Characteristics and Compositions of a Rapid Turbidimetric Assay for Zein," *J. Agr. Food Chem.*, 22:318–323 (1974).

(List continued on next page.)

*Primary Examiner*—Deborah D. Carr
(74) *Attorney, Agent, or Firm*—Leydig, Voit & Mayer, Ltd.

(57) ABSTRACT

Corn oil and corn meal obtained from high oil corn are included in useful products. The corn oil is extracted from the high oil corn to form the corn meal. The corn oil generally comprises levels of nutrients not found in commercially available corn oils, since most or all of the corn grain, rather than just the germ, is exposed to the extraction process. The corn grain generally includes the steps of flaking corn grain having a total oil content of at least about 6 wt. % and extracting a corn oil from the flaked corn grain. The corn oil is useful for making nutritionally enhanced edible oil or cooking oil, lubricants, biodiesel, fuel, cosmetics and oil-based or oil-containing chemical products. The extracted corn meal is useful for making enhanced animal feed rations, snack food, blended food products, cosmetics, and fermentation broth additive.

1 Claim, No Drawings

OTHER PUBLICATIONS

AOCS Recommended Practice Ba 2b–82 (1997).
AOCS Recommended Practice Ba 4e–93 (1999).
AOCS Recommended Practice Ba 6–84 (1997).
AOCS Recommended Practice Ba 3–38 (1997).
AOCS Recommended Practice Ca 5a–40 (1997).
AOCS Official Method Ca 12–55 (1997).
AOCS Official Method Cc13b–45 (2000).
Standard Analytical Methods of the Member Companies of the Corn Refiners Associaten, Inc., Standard 6–3–57 (1986).
XP–002199802, DuPont Quality Grains (1996).

PRODUCTS COMPRISING CORN OIL AND CORN MEAL OBTAINED FROM HIGH OIL CORN

The present application is a continuation-in-part of copending U.S. patent application Ser. No. 09/637,843, filed Aug. 10, 2000, which was a continuation-in-part of application Ser. No. 09/249,280, filed Feb. 11, 1999, now U.S. Pat. No. 6,313,328 the entire disclosures of which are hereby incorporated by reference.

FIELD OF THE INVENTION

The present invention relates to products that are derived from oil and meal extracted from corn having an oil content of about 6 wt. % or more.

BACKGROUND OF THE INVENTION

Corn, *Zea mays* L., is grown for many reasons including its use in food and industrial applications. Corn oil and corn meal are two of many useful products derived from corn.

Commercial processing plants utilizing conventional methods for extracting corn oil from conventional corn separate the corn seed into its component parts, e.g., endosperm, germ, tipcap, and pericarp, and then extract corn oil from the corn germ fraction. Corn germ produced by wet or dry milling is processed either by pressing the germ to remove the oil or by flaking the germ and extracting the oil with a solvent. In both processes, because the germ was separated from the remainder of the kernel, many or all of the valuable components of the endosperm fraction are absent from the oil.

A corn-based feed product known as hominy feed is obtained from the dry milling process and is a mixture of corn bran, corn germ, and endosperm, and has a minimum of about 4 wt. % oil. Several steps including cracking, grinding, sieving, and blending are required to manufacture hominy feed and the resulting particle size of hominy feed is small relative to meal made by the extraction method described herein.

Industry and health advocates are continually in search of more nutritious products derived from corn, since products derived from conventional corn lack some desired nutritional components. Thus, there exists a need for improved products derived from corn oil and corn meal.

BRIEF SUMMARY OF THE INVENTION

Finished products containing corn oil and/or corn meal obtained from conventional corn include, for example, cooking oil, animal feed, paper and paper products, numerous food products such as salad dressings, extruded and/or puffed snack foods, products containing corn sweeteners, cereals, chips, puddings, candies, and breads.

One aspect of the invention provides a nutritious animal feed comprising the corn meal remaining after extraction of oil from high oil corn having an oil content of about 6 wt. % or greater. The animal feed can comprise other nutritious products such as vitamins, minerals, high oil seed-derived meal, meat and bone meal, salt, amino acids, feather meal, and many others used in the art of feed supplementation. The animal feed composition can be tailored for particular uses such as for poultry feed, swine feed, cattle feed, equine feed, aquaculture feed, pet food and can be tailored to animal growth phases. Particular embodiments of the animal feed include growing broiler feed, swine finishing feed, and poultry layer finishing feed. Feed products can be made with the extracted corn meal that will have a higher relative percentage of protein and lower relative percentage of oil than similar products made with conventional corn.

Some embodiments of the invention include those wherein: 1) the corn meal has a fiber content of about 3%, a starch content of about 65%, and a protein content of about 12%, at a moisture content of about 10%; 2) the high oil corn grain has a total oil content of at least about 6 wt. %, at least about 7 wt. %, at least about 8 wt. %; at least about 10 wt. %, at least about 12 wt. %, at least about 14 wt. %, or from about 7 wt. % to about 30 wt. %; 3) the corn grain being flaked is whole corn grain or cracked corn grain; 4) the corn grain has been subjected to an oil extraction process such as solvent extraction, hydraulic pressing, or expeller pressing, aqueous and enzyme extraction; 5) the high oil corn grain has a total protein content of at least about 7 wt. %, at least about 9 wt. %, at least about 11 wt. %, or from about 7 wt. % to about 20 wt. %; 6) the high oil corn grain has a total lysine content of at least about 0.15 wt. %, at least about 0.5 wt. %, or from about 0.25 wt. % to about 2.0 wt. %; and/or 7) the high oil corn grain has a total tryptophan content of at least about 0.03 wt. %, at least about 0.20 wt. %, or from about 0.03 wt. % to about 2.0 wt. %.

A preferred embodiment provides a method of obtaining corn oil and solvent extracted corn meal (SEC) from high oil corn. The method provides steps of: 1) tempering the corn; 2) cracking the tempered corn; 3) conditioning the cracked corn; 4) flaking the conditioned corn; 5) extracting the flaked corn; and 6) removing the solvent from both the corn oil and solvent extracted corn meal. The method provides a greater overall content of corn oil and concentrates the proteins in the meal. Moreover, solvent extractable pigments can be removed from the SEC.

Another aspect of the invention provides a corn oil-based product comprising corn oil obtained by extraction of at least the endosperm and germ of high oil corn. The corn oil-based product can comprise other components such as vinegar, spices, vitamins, salt, hydrogen (for forming hydrogenated products), and water. The corn oil used in the products of the invention will generally contain a higher proportion of β-carotene, xanthophylls or tocotrienol than similar products made with corn oil extracted from conventional corn employing conventional methods. The corn oil, used in the products of the invention, is generally produced by exposing the entire corn grain, the cracked corn grain or the flaked corn grain to extraction without separation of the germ from the endosperm. Therefore, the solvent-extractable nutrients present in the endosperm are extracted into the corn oil that has been extracted from the germ and endosperm. Products that can be made with the oil prepared as described herein include, but are not limited to, salad dressings, cooking oils, margarines, spray-coated food or feed products, breads, crackers, snack foods, lubricants, and fuels.

Other embodiments of the invention include those wherein: 1) high oil corn grain is cracked, conditioned, flaked and extracted with a solvent; 2) the high oil corn grain has a total oil content of at least about 6 wt. %, at least about 7 wt. %, at least about 8 wt. %; at least about 10 wt. %, at least about 12 wt. %, at least about 14 wt. %, or from about 7 wt. % to about 30 wt. %; 3) the corn oil is extracted by pressing cracked corn; 4) the corn oil is extracted by subjecting flaked corn grain to a solvent-based extraction process; 5) the solvents used to extract miscible or soluble substances from the flaked grain include all forms of commercially available hexanes, isopropyl alcohol, ethanol, supercritical carbon dioxide or mixtures thereof; 6) the extracted corn oil is provided as miscella; 7) the corn oil is refined by additional processing; and 8) the corn oil is extracted by subjecting flaked corn grain to hydraulic pressing and/or expeller pressing, aqueous and/or enzyme extraction processes.

A third aspect of the invention provides a method of using extracted corn meal in an animal feed ration comprising the step of: 1) providing an extracted corn meal prepared by at least flaking high oil corn to form flaked corn and extracting the flaked corn to remove a portion of the corn oil therefrom; and 2) including the extracted corn meal in an animal feed ration.

A fourth aspect of the invention provides a method of using an extracted corn oil in a food product comprising the steps of: 1) providing an extracted corn oil obtained by at least flaking high oil corn to form flaked corn and extracting the flaked corn to remove a portion of the corn oil therefrom and form the extracted corn oil; and 2) including the extracted corn oil in a food product.

A fifth aspect of the invention provides a method of using extracted corn oil as a feedstock in an oil refining process. The method comprises the steps of: 1) providing an extracted crude corn oil obtained by at least flaking high oil corn to form flaked corn and extracting the flaked corn to remove a portion of the corn oil therefrom and form the extracted crude corn oil; and 2) including the extracted crude corn oil in a raw material stream of an oil refining process.

A sixth aspect of the invention provides various methods of forming extracted blended meals. A first embodiment of this aspect of the invention provides a method of forming an extracted blended meal comprising an extracted meal obtained from high oil corn and one or more other oilseed meals, the method comprising the step of: 1) combining high oil corn grain and one or more other oilseed grains to form a grain mixture; and 2) subjecting the grain mixture to flaking and an extraction process to remove oil therefrom and form the extracted blended meal. A second embodiment provides a method comprising the steps of: 1) combining a cracked and conditioned high oil corn with another cracked and conditioned oilseed to form a conditioned mixture; 2) flaking the conditioned mixture to form a flaked mixture; and 3) subjecting the flaked mixture to an extraction process to remove oil therefrom and form the extracted blended meal. A third embodiment provides a method comprising the steps of: 1) combining a cracked, conditioned and flaked high oil corn with a cracked, conditioned and flaked other oilseed to form a flaked mixture; and 2) subjecting the flaked mixture to an extraction process to remove oil therefrom and form the extracted blended meal. A fourth embodiment provides a method comprising the step of combining an extracted corn meal with one or more extracted other oilseed meals to form a blended meal, wherein the extracted corn meal has been obtained by at least flaking and extracting high oil corn to form the extracted corn meal. A fifth embodiment provides a blended extracted meal product prepared according to any one of the above-described methods.

A seventh aspect of the invention provides a method of using extracted corn oil as an ingredient in cosmetic applications. The method comprises the steps of: 1) providing an extracted crude corn oil obtained by at least flaking high oil corn to form flaked corn and extracting the flaked corn to remove a portion of the corn oil therefrom and form the extracted crude corn oil; and 2) including the extracted crude corn oil in a cosmetic product. These types of cosmetics include but are not limited to lipstick and eye liner.

Another aspect of the invention provides the use of a corn meal in an animal feed or human food, wherein the corn meal is obtained after extraction of corn oil from whole kernels of high oil corn.

Yet another aspect of the invention provides the use of a corn oil in an animal feed or human food, wherein the corn oil is obtained by extraction from whole kernels of high oil corn.

Other aspects of the invention provide corn oil-containing and/or corn meal-containing products made by the processes described herein.

Unless otherwise defined, all technical and scientific terms and abbreviations used herein have the same meaning as commonly understood by one of ordinary skill in the art to which this invention pertains. Although methods and materials similar or equivalent to those described herein can be used in the practice of the present invention, suitable methods and materials are described below without intending that any such methods and materials limit the invention described herein. All patents publications and official analytical methods referred to herein are incorporated by reference in their entirety. Additional features and advantages of the invention will be apparent from the following description of illustrative embodiments of the invention and from the claims.

BRIEF DESCRIPTION OF THE DRAWINGS

FIG. 1 illustrates the total amount of ethanol produced and dextrose consumed by yeast grown on yellow dent corn (YD), yellow dent meal (YDM), high oil corn (HOC), and high oil corn meal (HOCM).

FIG. 2 illustrates the pH values of yeast cultures containing yellow dent corn (YD), yellow dent meal (YDM), high oil corn (HOC), and high oil corn meal (HOCM).

DETAILED DESCRIPTION OF THE INVENTION

It has been discovered that corn oil can be rapidly and efficiently extracted on a commercial-scale from corn grain having increased oil content by optionally cracking and then conditioning, and flaking the corn grain and extracting a corn oil. Useful corn grain for the novel flaking oil processing method has a total oil content greater than about 6 wt. %. Increases in the oil content of corn grain may increase flaking efficiency during processing. Suitable flaking equipment and methods include conventional flaking equipment and methods used for flaking soybean and other similar oilseed types. Suitable extracting equipment and methods may include conventional methods used for extracting oil from soybean flakes and other similar oilseed types.

High oil corn seed or "grain" harvested from any of several different types of corn plants is useful in the invention. These types of corn plants are, for example, hybrids, inbreds, transgenic plants, genetically modified plants or a specific population of plants. Enhanced extracted meals can be made by subjecting enhanced high oil corn to the extraction process described herein. Useful corn grain types include, for example, flint corn, popcorn, flour corn, dent corn, white corn, and sweet corn. The high oil corn grain can be in any form including whole corn, cracked corn, or other processed corn or parts thereof that are amenable to flaking but different from the standard methods of germ separation employed in dry and wet milling for subsequent recovery of oil from the germ.

As used herein, the terms "whole kernel" or "whole corn" mean a kernel that has not been separated into its constituent parts, e.g. the hull, endosperm, tipcap, pericarp, and germ have not been purposefully separated from each other. The whole corn may or may not have been ground, crushed, cracked, flaked, or abraded. Purposeful separation of one corn constituent from another does not include random separation that may occur during storage, handling, transport, crushing, flaking, cracking, grinding or abrading. A purposeful separation of the constituent part is one wherein at least 50% of one constituent, e.g., germ, has been separated from the remaining constituents.

As used herein, the term "high oil corn" refers to corn grain comprising at least about 6 wt. % or greater, preferably at least about 7 wt. % or greater, and preferably at least about 8 wt. % or greater oil. A high oil corn has an elevated level of oil as compared to conventional yellow dent corn, which has an oil content of about 3 wt. % to about 5 wt. %. Additionally, the total oil content of corn grain suitable for the invention can be, for example, grain having an oil content at least about 9 wt. %, at least about 11 wt. %, at least about 12 wt. %, at least about 15 wt. %, at least about 18 wt. %, at least about 20 wt. %, from about 8 wt. % to about 20 wt. % oil, from about 10 wt. % to about 30 wt. % oil, or from about 14 wt. % to about 30 wt. %, and values within those ranges. Although the oil content can be determined at any moisture content, it is acceptable to normalize the oil content to a moisture content of about 15.5%.

High oil corn useful in making the oil and meal described herein are available from Cargill, Incorporated (Minneapolis, Minn.) or Pfister Hybrid Corn Co. (El Paso, Ill.). Other suitable high oil corn includes the corn populations known as Illinois High Oil (IHO) and Alexander High Oil (Alexo), samples of which are available from the University of Illinois Maize Genetics Cooperative—Stock Center (Urbana, Ill.).

Corn grain having an elevated total oil content is identified by any of a number of methods known to those of ordinary skill in the art. The oil content of grain, including the fat content of a meal extracted from the grain, can be determined using American Oil and Chemical Society Official Method, 5$^{th}$ edition, March 1998, ("AOCS method Ba 3-38"). AOCS method Ba 3-38 quantifies substances that are extracted by petroleum ether under conditions of the test. The oil content or concentration is the weight percentage of the oil with respect to the total weight of the seed sample. Oil content may be normalized and reported at any desired moisture basis.

Other suitable methods for identifying high oil corn grain are described herein. According to one method, corn ears are selected using a near infrared (NIR) oil detector to select corn ears having corn kernels with elevated oil levels. Likewise, an NIR detector can also be used to select individual corn kernels having elevated levels of corn oil. However, selecting individual ears and/or kernels having elevated oil content may not be cost effective in identifying high oil kernels suitable for processing using methods described herein. Generally, corn seed producing corn plants that yield grain having elevated total oil concentrations is planted and harvested using known farming methods. Methods for developing corn inbreds, hybrids, transgenic species and populations that generate corn plants producing grain having elevated oil concentrations are known and described in Lambert (Specialty Corn, CRC Press Inc., Boca Raton, Fla., pp. 123–145 (1994).

One of the suitable high oil corns used as a raw material for preparing the corn oil and corn meal used in the invention has a nutrient profile as shown in Table 1. Amounts are expressed on an "as is" or "as fed" moisture level. Protein, oil, and starch levels can vary in a number of possible combinations in the high oil corn used as a raw material for meal and oil used in the invention. Acceptable amounts of moisture, oil, protein, starch, lysine, and tryptophan are illustrated in Table 1. However, additional combinations, such as 12 wt. % protein and 12 wt. % oil, not shown as indicated amounts in the table are within the scope and range of corn grain to be used to produce oil and meal used in the invention.

TABLE 1

| Component | Amount 1 (wt. %) | Amount 2 (wt. %) | Amount 3 (wt. %) | General Amount (wt. %) |
| --- | --- | --- | --- | --- |
| Moisture | 14 | 14 | 14 | 5–45 |
| Oil | 8 | 12 | 20 | 6–30 |
| Protein | 9 | 9 | 17 | 5–20 |
| Starch | 61 | 54 | 41 | 35–80 |
| Lysine | 0.35 | 0.50 | 1.0 | 0.15–2.0 |
| Tryptophan | 0.088 | 0.11 | 0.15 | 0.03–2.0 |

Another suitable high oil corn used as a raw material for preparing the corn oil and corn meal used in the invention has a nutrient profile as shown in Table 2. Amounts are expressed on an "as is" or "as fed" moisture level. The amounts shown in Table 2 are exemplary for a corn grain having 12 wt. % oil and 9 wt. % protein.

TABLE 2

| Component | Amount (wt. %) | General Amount (wt. %) |
| --- | --- | --- |
| Moisture | 14 | 5–45 |
| Oil | 12 | 6–30 |
| Protein | 9 | 5–20 |
| Starch | 65 | 35–80 |
| Fiber | 3 | 1–5 |
| Ash | 1.18 | 0.59–4.72 |
| Lysine | 0.33 | 0.2–2.0 |
| Tryptophan | 0.09 | 0.03–2.0 |
| Methionine | 0.25 | 0.13–1.00 |
| Total Sulfur Amino Acids | 0.46 | 0.23–1.84 |
| Valine | 0.45 | 0.23–1.80 |
| Isoleucine | 0.34 | 0.17–1.36 |
| Arginine | 0.45 | 0.23–1.80 |
| Threonine | 0.34 | 0.17–1.36 |
| Leucine | 1.03 | 0.52–4.12 |
| Histidine | 0.27 | 0.14–1.08 |
| Phenylalanine | 0.44 | 0.22–1.76 |
| Alanine | 0.70 | 0.35–2.80 |
| Aspartic | 0.74 | 0.37–2.96 |
| Cystine | 0.22 | 0.11–0.88 |
| Glutamic | 1.9 | 0.95–7.6 |
| Glycine | 0.46 | 0.23–1.84 |
| Proline | 0.86 | 0.43–3.44 |
| Tyrosine | 0.06 | 0.03–0.54 |
| Serine | 0.46 | 0.23–1.84 |

Table 3 shows amino acid levels (based on a corn grain moisture content of about 10%) of two high oil corn grain samples and normal yellow corn grain. The oil and protein levels of high oil corn sample 1 (HOC 1) were 13.3 wt. % and 10.7 wt. % respectively, expressed on a dry matter basis. The oil and protein levels of high oil corn sample 2 (HOC 2) were 13.0 wt. % and 11.2 wt. % respectively, expressed on a dry matter basis. For comparison, normal yellow corn grain has about 4.2 wt. % oil and about 9.2 wt. % protein on a dry matter basis.

TABLE 3

| Amino Acid | HOC 1 (%) | HOC 2 (%) | Yellow Corn (%) |
|---|---|---|---|
| Aspartic Acid | 0.71 | 0.68 | 0.48 |
| Threonine | 0.33 | 0.30 | 0.19 |
| Serine | 0.37 | 0.27 | 0.19 |
| Glutamic Acid | 1.84 | 1.79 | 1.16 |
| Proline | 0.83 | 0.78 | 0.52 |
| Glycine | 0.40 | 0.42 | 0.24 |
| Alanine | 0.77 | 0.74 | 0.47 |
| Valine | 0.51 | 0.52 | 0.33 |
| Cystine | 0.21 | 0.23 | 0.16 |
| Methionine | 0.46 | 0.47 | 0.39 |
| Isoleucine | 0.30 | 0.30 | 0.20 |
| Leucine | 1.19 | 1.08 | 0.74 |
| Tyrosine | 0.11 | 0.11 | 0.06 |
| Phenylalanine | 0.52 | 0.48 | 0.32 |
| Tryptophan | 0.06 | 0.07 | 0.05 |
| Lysine | 0.34 | 0.38 | 0.21 |
| Histidine | 0.29 | 0.29 | 0.18 |
| Arginine | 0.45 | 0.48 | 0.28 |

High oil corn is generally subjected to an extraction process as described herein to provide the enhanced corn oil and corn meal to be included in the finished products of the invention. As used herein, the term "finished product" or "product" refers to an article or manufacture made by combining the corn oil and/or corn meal of the invention with a variety of other ingredients. The specific ingredients included in a product will be determined according to the ultimate use of the product. Exemplary products include animal feed, raw material for chemical modification, biodegradable plastic, blended food product, edible oil, cooking oil, lubricant, biodiesel, snack food, cosmetics, and fermentation process raw material. Products incorporating the meal described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multivitamin supplements, diet drinks, and cereal foods.

For example, starting with a single corn type (e.g., 12 wt. % oil and 9 wt. % protein), more than one corn meal type can be made to meet certain nutritional requirements. The significance of this flexibility relates to the nutrient density within feed products and to dietary requirements of animals. One significant advantage of the use of this type of high oil corn and extraction process is that an extracted corn meal can be made to have a specific oil level depending on the extent of oil extraction. Once the oil is removed from the flakes, the remaining corn meal has a nutrient density for protein, amino acids, and other nutrients not removed by the process, greater or different than normal corn grain and greater than that of the starting corn, e.g., 12 wt. % oil, 9 wt. % protein.

According to one extraction process used in preparing the corn oil and corn meal as described herein, whole grain high oil corn is optionally tempered, optionally cracked, and then conditioned and flaked. After flaking, the flaked corn is extracted as described herein.

Whole grain corn is optionally tempered before the extraction process. As used herein, the term "tempering" is used interchangeably with the terms "heat soaking" or "steaming" and is a means to uniformly distribute the added moisture through the entire corn kernel. Any tempering method known in the art is acceptable. In general, the corn is steeped in an appropriate amount of water for any suitable length of time, such as at least 20 minutes, preferably at least 4 hours, preferably at least 6 hours, more preferably at least 12 hours, or most preferably at least 24 hours. After the corn has steeped for the desired length of time, its moisture content is retested. The corn may be stored for short periods of time, but is preferably processed within 24 hours and most preferably processed immediately.

Whole grain corn is also optionally cracked. In a preferred embodiment, the whole high oil corn is cracked after tempering yet before conditioning. The high oil corn may be cracked by passing the whole grain corn between two rollers with corrugated teeth spinning toward each other spaced by a defined gap, and/or passing through a grind mill where a rotating toothed disk spins at an adjustable distance from a stationary disk, and/or the use of a hammermill where two rotating metal "hammer" like devices spinning next to one another. Methods for cracking corn or high oil seeds are described in Watson, S. A. & P. E. Ramstad, ed. (1987, Corn: Chemistry and Technology, Chapter 11, American Association of Cereal Chemist, Inc., St. Paul, Minn.), the disclosure of which is hereby incorporated by reference in its entirety. A "cracked" corn is a corn that has undergone the above-described cracking process.

Regardless of whether or not the corn is cracked, it is conditioned using methods known to those of ordinary skill in the art and/or methods described herein. As used herein, the term "conditioning" refers to a process by which the corn kernel is softened or plasticized to render it more pliable and amenable to the flaking and extraction processes. Conditioning may include the addition of steam (saturated and/or non-saturated steam) and/or water to the high oil corn. This is done by the use of a rotary conditioner. During the steam addition process, both the temperature and the moisture levels are elevated. The temperature ranges between about 140° F. and about 210° F. and the moisture is increased by about 1% to about 15%.

The high oil corn grain is then flaked to any useful size. As used herein, the term "flaking" refers to a process by which corn grain is passed one or more times through flaking rollers to produce flakes. The flaked corn may have a final flake thickness of about $5/1000$ to $100/1000$ of an inch (~0.12 mm to 2.0 mm) or preferably about 0.01 inches (0.25 mm), although other thicknesses may also be used. Useful flake thickness may depend on external limiting parameters such as the oil content of the corn, the moisture content, the corn type, e.g., dent or flint, and the oil extractor type. Suitable methods for flaking high oil corn are detailed herein and in D. R. Erickson, Practical Handbook of Soybean Processing Utilization (1995, AOCS Press), the entire disclosure of which is hereby incorporated by reference. Suitable flaking methods also include those known to those of ordinary skill in the art of oilseed processing.

After the corn is tempered, cracked and/or conditioned and flaked, the flaked corn is subjected to an extraction process to extract oil to form an extracted corn meal (ECM). Corn oil is extracted from flaked grain by one or more extraction steps using any extraction method. Generally, substantially, or about all of the oil is extracted in a single extraction process. Useful extraction methods include solvent extraction, continuous solvent extraction, hydraulic pressing, expeller pressing, aqueous and/or enzyme extraction. Useful solvents for solvent extraction include, for example, all forms of commercially available pentane, hexanes, isopropyl alcohol, ethanol, supercritical carbon dioxide, combinations thereof, and other similar solvents. For example, corn oil can be extracted from flaked grain using a hexane-based solvent extractor. Solvent extractors can include both percolation and immersion type extractors.

In a preferred embodiment, a continuous solvent extraction process allows the flaked corn to remain in contact with the solvent for at least 10 minutes, preferably at least 30 minutes, more preferably at least 60 minutes, and most preferably at least 90 minutes.

Materials removed from solvent-based extractors include wet flakes and miscella. A miscella is a mixture of extracted oil and solvent. The wet flakes are the materials that remain after some or all of the solvent-soluble material has been extracted. Wet flakes also contain a quantity of solvent. Solvent is reclaimed from both the miscella and wet flakes using methods such as rising film evaporation, or drying, and raising the temperature using equipment such as flash tanks and/or desolventiser/toasters. For example, heat is applied to the wet flakes or miscella under atmospheric pressure, under elevated pressure, or under vacuum to evaporate the solvent. The evaporated solvent is then condensed in a separate recovery system, and optionally dewatered and recycled to the extractor.

Desolventized miscella is commonly termed crude oil, which can be stored and/or undergo further processing. Crude oil can be refined to produce a final oil product. Methods for refining crude oil to obtain a final oil are known to those of ordinary skill in the art. Hui (1996) provides a thorough review of oils and oilseeds (Bailey's Industrial Oil and Fat Products, Fifth Ed., Vol. 2, Wiley and Sons, Inc., New York, 1996). Chapter three of Hui (pp. 125–158), the disclosure of which is hereby incorporated by reference, specifically describes corn oil composition and processing methods. Crude oil isolated using the flaking methods described herein is of a high quality but can be further purified as needed using conventional oil refining methods.

In a preferred embodiment, the present invention relates to a method of recovering lighter particles, such as fines, during the processing of high oil corn. As used herein, the term "fines" means any particle of the corn process that passes through a #18 sieve having a 1.00 mm opening as defined in ASTM E-11 specifications. The recovery of the particles may occur before, after, or during any step in the process, such as during the moisture removal step, during the cracking step or before or after the flaking process. In general, fines are recovered by passing a current of gas (e.g., air, nitrogen, argon) over the corn at a suitable velocity and direction such that smaller and lighter particles are carried away in the stream, leaving behind larger and heavier particles. Alternatively, lighter particles can be separated from heavier particles using a liquid spray (e.g., water, process water). The liquid is applied broadly enough so as to physically eliminate the lighter, airborne particles. The liquid spray can include components that add value to the end product, such as vitamins, minerals, enzymes, and combinations thereof. In addition, the liquid spray can further comprise a caustic liquid. Regardless of the separation method, these fine particles can be captured or recovered by any method known in the art such as using a baghouse. Preferably, the recovered lighter particles can be reintroduced into starch-containing product streams for the recovery of starch. Additionally the fines may be sold as an animal feed.

Corn endosperm includes some valuable components such as carotenoids, lutein, and zeaxanthin. Carotenoids in grains are classified into two general groups, the carotenes and the xanthophylls. The carotenes are important because they are vitamin A precursors. Blessin et al. (*Cereal Chemistry*, 40, 582–586(1963)) found that over 90% of the carotenoids, of which beta-carotene is predominant, are located in the endosperm of yellow dent corn and less than 5% are located in the germ. Vitamin A is derived primarily from beta-carotene.

Another group of valuable components found in the endosperm includes the tocotrienols. Grams et al. (1970) discovered that in corn, tocotrienols were found only in the endosperm, whereas the germ contained most of the tocopherols. Tocotrienols can be extracted from plant material using various solvents. Processes for recovering tocotrienols from plant material are described by Lane et al. in U.S. Pat. No. 5,908,940, the entire disclosure of which is incorporated by reference.

Accordingly, the process described herein provides a nutritionally enhanced corn oil enriched with lutein, zeaxanthin, and/or beta-carotene and optionally one or more other nutritional components.

Oil-based products made with corn oil obtained by the extraction method described herein can contain higher levels of important nutrients than similar products made with corn oil produced by conventional methods. The corn oil obtained by the extraction methods described herein will include the corn oil from the germ and endosperm, and one or more other components extracted from the rest of the kernel. The one or more other components can be oil from the endosperm, tocotrienols, tocopherols, carotenoids, carotenes, xanthophylls, and sterols.

Tocopherols (vitamin E) and vitamin A are antioxidants and fat-soluble vitamins. When included in the diet, both have demonstrated health benefits. Blending of oil of the present invention with other oils or substances to achieve an appropriate level of beta-carotene, vitamin E, and tocotrienols is deemed within the scope of the present invention. In some embodiments, extracted corn oil prepared as described herein comprises about 0.1 wt. % to about 0.5 wt. % of tocopherol.

Oil produced in accordance with the present invention also may include approximately a 200% to 300% increase in tocotrienol content over conventionally-produced crude corn oil. Using the method of optionally tempering, cracking and/or conditioning and/or flaking and extraction of high oil corn, the corn oil was extracted and was then analyzed for tocotrienol content. The actual minimum and maximum values for tocotrienol content will depend upon the particular high oil corn used.

The oxidative stability index (OSI), measured in hours, is a measure of an oil's relative stability toward oxidation. Generally, the greater the OSI, the less susceptible the oil is toward oxidation and the longer it takes to oxidize the oil under test or use conditions. In addition, the greater the content of unsaturated fatty acids present in the oil, the lower the OSI. Exemplary oils prepared according to the extraction method described herein generally possess OSI values ranging from about 10–22 hours.

Extraction of carotenes and xanthophylls and other pigments is described in detail by Blessin (Cereal Chemistry, 39, 236–242 (1962); the entire disclosure of which is incorporated by reference). Combinations of solvents, primarily ethanol and hexanes, can be used to extract carotenes and xanthophylls from corn. Ethanol, hexanes, other solvents combinations, and ratios thereof may be used to produce oil of the present invention on a commercial scale.

Exemplary embodiments of the crude oil obtained according to the extraction method described herein generally possess the partial composition profile featured in Table 4.

TABLE 4

| Component | Exemplary Extracted High Oil Corn | Extracted High Oil Corn (Range) |
|---|---|---|
| FFA (%) | 1.45 | 0.7–3.00 |
| C16:0 | 11.4 | 10–14 |
| C18:0 | 2.1 | 1.5–3.5 |
| C18:1, cis | 33 | 26–50 |
| C18:1, trans | | |
| C18:2, cis | 50 | 42–60 |
| C18:2, trans | | |
| C18:3 | 0.8 | 0.6–1.6 |
| Phosphorus (ppm) | 190 | 100–400 |
| Total Tocopherols (ppm) | 0.13 | 0.1–.50 |

Fatty acids generally found in the corn oil generally include palmitic, stearic, oleic, linoleic and linolenic acids.

The crude oil prepared according to the methods described herein can be subsequently partially or completely hydrogenated. Suitable methods for partially or completely hydrogenating oil are described in D. R. Erickson, Practical Handbook of Soybean Processing Utilization (1995, AOCS Press), the entire disclosure of which is hereby incorporated by reference.

When making oil-based products according to the invention, those products can include conventional corn oil, soy oil, canola oil, olive oil, palm oil, sunflower oil, safflower oil, antioxidant, flavoring, hydrogenated oil, partially hydrogenated oil and/or animal fat. By mixing the corn oil herein with one or more other oils, blended oil products are made. The corn oil-based products can also include materials such as food additives, salt, fat, food colors, β-carotene, annatto extract, curcumin or tumeric, β-apo-8'-carotenal and methyl and ethyl esters thereof, natural or synthetic flavors, antioxidants, propyl gallate, butylated hydroxytoluene, butylated hydroxyanisole, natural or synthetic tocopherols, ascorbyl palmitate, ascorbyl stearate, dilauryl thiodiproprionate, antioxidant synergists, citric acid, sodium citrate, isopropyl citrate, phosphoric acid, monoglyceride citrate, anti-foaming agent, dimethyl polysiloxane, crystallization inhibitor, oxystearin, amino acids, vitamin, minerals, carbohydrates, sugars, herbs, spices, acidity regulators, firming agents, enzyme preparations, flour treatment agents, viscosity control agents, enzymes, lipids, and/or vegetable or animal protein. Additionally, these edible products can be enhanced or enriched with protein supplements containing utilizable protein. An exemplary food product such as a breakfast cereal could include ingredients such as meal of the invention, wheat and oat flour, sugar, salt, corn syrup, milled corn, dried fruit, vitamin C, B vitamins, folic acid, baking soda, and flavorings.

Other exemplary oil-based products that can comprise the oil prepared herein include food oil, cooking oil, edible oil and blended oil.

Equipment used for the extraction of oil from oilseeds, such as soybean and canola, can be used to prepare the corn oil and extracted corn meal described herein. Useful commercial-scale oilseed flakers can be obtained from French Oil Mill Machinery Company, Piqua, Ohio; Roskamp Champion, Waterloo, Iowa; Buhler, based in Switzerland with offices in Plymouth, Minn.; Bauermeister, Inc., Germany; Consolidated Process Machinery Roskamp Company, on the world wide web at http://www.cpmroskamp.com, and Crown Iron Works, Minneapolis, Minn.

Commercial-scale methods and equipment are sufficient for extracting corn oil from at least about 1 ton of corn per day. In some embodiments, the capacity of commercial-scale operations ranges from about 100 tons of corn per day to about 3000 tons of corn per day, or the capacity ranges from about 700 tons of corn per day to about 1700 tons of corn per day. Commercial-scale operations that process greater than about 3000 tons of corn per day are also sufficient.

Corn oil or corn meal quality is determined by evaluating one or more quality parameters such as the oil yield, phosphorus content, free fatty acid percentage, the neutral starch percentage, protein content, and moisture content. Any method can be used to calculate one or more of the quality parameters for evaluating the oil or meal quality.

The phosphorus concentration of crude oil can be determined using AOCS method Ca 12-55. AOCS method Ca 12-55 identifies the phosphorus or the equivalent phosphatide zinc oxide, followed by the spectrophotometric measurement of phosphorus as a blue phosphomolybdic acid complex. AOCS method Ca 12-55 is applicable to crude, degummed, and refined vegetable oils. The phosphorus concentration is converted to phospholipid concentration, i.e., gum concentration, by multiplying the phosphorus concentration by 30. In some embodiments, corn oil produced according to the invention includes about 100–400 ppm of phosphorus.

The free fatty acid percentage of oil can be determined using AOCS method Ca 5a-40. AOCS method Ca 5a-40 identifies the free fatty acids existing in the oils sample. AOCS method Ca 5a-40 is applicable to all crude and refined vegetable oils, marine oils, and animal fats. The neutral oil loss during processing is determined by adding the gum percentage and the free fatty acid percentage together. The amount of free fatty acid obtained in the extracted corn oil will depend upon the amount of fatty acids found within the high oil corn from which the oil was extracted. In some embodiments, the free fatty acid content of the extracted oil ranges from about 0.70 wt. % to 3.00 wt. %

Oil color can be determined using AOCS ethod Cc 13b-45. AOCS method Cc 13b-45 identifies the color of an oil sample by comparing the oil sample with known color characteristics. AOCS method Cc 13b-45 is applicable to fats and oils provided no turbidity is present in the sample. Color values e evaluated qualitatively by visual inspection of the oil. Generally, visual inspection results in an oil being classified as a light oil or a dark oil compared to a known oil color. Color values are quantitated by determining a red color value and a yellow color value using the AOCS method Cc 13b-45. Typically, crude corn oil isolated using conventional dry milling methods has a red color value ranging from about 7 to about 10 and a yellow color value ranging from about 60 to about 70. It is expected that corn oils isolated using cracking methods described herein will have oil colors that qualitatively are considered light and generally are lighter than crude corn oil derived from wet or dry milling techniques. The yellow color values may range from about 60 to about 70 and red color values may range from about 7 to about 10, as determined by AOCS Method Cc 13b-45.

The extracted corn oil can be used as a raw material for chemical modification, a component of biodegradable plastic, a component of a blended food product, a component of an edible oil or cooking oil, lubricant or a component thereof, biodiesel or a component thereof, a component of a snack food, a fermentation process raw material, and a component of cosmetics. Since the oil obtained by the extraction process herein has one or more components obtained from non-germ parts of the corn kernel, the oil is enhanced. In some embodiments, the oil will have an oleic range from about 20% to 80%, or preferably 25% to 50%, whereas normal corn has about 25% to 40% oleic acid in the oil. When making blended oils with the extracted oil, the blending can be done before, during or after the extraction process.

Biodiesel can be produced using the extracted corn oil of the invention. Biodiesel is a general term used for a variety of ester-based oxygenated fuels. Biodiesel produced today is a mixture of fatty acid methyl esters produced by methylating refined vegetable oil. Refined oil is preferable to crude oil or spent fryer oil due primarily to the quality of the glycerol by-product. The main drawbacks with previous biodiesel products and related vegetable oil lubricants are low temperature properties and reactivity toward oxidation and polymerization. A preferred biodiesel product comprises a low cloud point, reduced stearic and polyunsaturated fatty acid content, and high oleic acid content. Pour point correlates with low temperature properties and is influenced by the saturated fatty acid content of the oil. Polyunsaturated fatty acids are more susceptible to oxidation and polymerization reactions.

Solvent-extracted corn (SEC) oil exhibits improved cloud point performance over soy, while exhibiting similar chemical stability.

TABLE 5

| Oil | % Palmitic (16:0) | % Stearic (18:0) | % Oleic (18:1) | % Linoleic (18:2) | % Linolenic (18:3) | % Erucic (22:1) |
| --- | --- | --- | --- | --- | --- | --- |
| Rape | 3 | 1 | 14 | 12 | 7 | 49 |
| Canola | 4 | 1 | 60 | 20 | 9 | 2 |
| Soy | 8–10 | 4 | 19–28 | 53–56 | 6–10 | 0 |
| SEC | 11 | 2 | 27 | 56 | | |

SEC oil corn can be further processed to form lubricants such as by published procedures practiced currently in the industry (see, e.g., U.S. Pat. No. 6,174,501).

Meal produced from the flaking and oil extraction process described herein is used to produce unique feed products. The corn meal used herein has been obtained after extraction of oil from whole kernels of high oil corn, wherein the kernel has not been separated into its constituent part, although the kernel may or may not have been ground, flaked, cracked, chipped, or abraded. The process of removing the oil from corn via extraction serves to concentrate the remaining nutrients such as protein and essential amino acids.

Feed products containing predominantly corn meal produced by extraction require less supplementation with protein from other sources such as soybeans than feed products containing predominantly normal corn grain. The meal, by virtue of the composition arising from the processing method, offers feed manufacturers flexibility to produce feeds that could otherwise not be made. Animal feed rations having unique physical properties such as bulk density, texture, pelletability, and moisture holding capacity and/or unique nutritional properties are created by including the extracted corn meal of the present invention as a component of said rations. The extracted corn meal isolated using flaking and extraction methods as described herein can, on its own, be a low-fat corn meal. Alternatively, it can be used in combination with other corn meals or nutritional components to make feed rations and food products. The extracted corn meal can also be combined with meals made from crops such as soybeans, canola, sunflower, oilseed rape, cotton, and other crops. The extracted corn meal can also be made from genetically modified corn and/or combined with meals made from transgenic oilseed grains to form an enhanced meal or enhanced product.

The extracted corn meal can be provided as a loose product or a pelleted product, optionally in combination with other components. For example, a pelleted product could include the extracted corn meal (by itself or in combination with other components) that has been pelleted and subsequently coated with zein protein. The corn meal can be included in blended meal products which can be provided in loose or pelleted form.

The feed rations prepared with the extracted corn meal will generally meet the dietary and quality standards set forth in the CODEX ALIMENTARIUS or by the National Research Council. The corn meal of the invention will generally comprise the components in the approximate amounts indicated in Table 6 below.

TABLE 6

| Component | Sample A Amount (%) | Sample B Amount (%) | Sample C Amount (%) |
| --- | --- | --- | --- |
| Moisture | 5–45 | 5–25 | 5–45 |
| Starch | 40–70 | 40–80 | 40–70 |
| Protein | 8–20 | 7–20 | 8–20 |
| Fat (Oil) | 0.75–6 | 0.75–6.0 | 0.75–12 |
| Crude Fiber | 2–4 | 2–4 | |
| Ash | 1.5–3 | 0.5–2.0 | |
| Fructose | 0.15–0.3 | | |
| Glucose | 0.2–0.5 | | |
| Sucrose | 1.5–2.5 | | |
| Lysine | | | 0.2–2.0 |
| Tryptophan | | | 0.03–2.0 |

The corn meals above may also further comprise unspecified amounts of the components for which no amounts have been indicated.

Varying levels of nutrients are required by different animals depending on species, age, and breed. Feed rations comprising different levels of nutrients are made by subjecting the high oil corn to different degrees of extraction, i.e., more oil is removed from the corn by subjecting it to extraction to a greater degree. Therefore, feed rations comprising the extracted corn meal of the invention can be made to include different amounts of fat, protein, and carbohydrates by controlling the extent to which the high oil corn is extracted. Table 7 details the amounts in which the indicated ingredients are present in animal feed rations comprising the extracted corn meal, the specific inclusion range being indicative of exemplary rations in which extracted corn meal is a main ingredient and the general inclusion range being indicative of rations in which one or more other ingredients, for example, carbohydrate-based energy sources such as sorghum, wheat, and/or other cereal grains or their by-products, or other non-cereal grain ingredients, may be included.

TABLE 7

| Ingredient | General Inclusion Range | Exemplary Inclusion Range |
| --- | --- | --- |
| Corn meal described herein | 2–95% | 50–90% |
| Oilseed Meal[1] | 3–35% | 10–30% |
| Meat and Bone Meal | 0–12% | 0–7% |
| Feather Meal | 0–6% | 0–4% |

TABLE 7-continued

| Ingredient | General Inclusion Range | Exemplary Inclusion Range |
| --- | --- | --- |
| Fat | 0–10% | 1–6% |
| Salt | 0.1–0.5% | 0.1–0.5% |
| Lysine | 0–0.4% | 0–0.4% |
| Methionine | 0–0.3% | 0–0.3% |
| Nutrient Premix | 0.01–1.0% | 0.01–1.0% |

[1]Oilseed meal can consist of, but is not limited to, soy, sunflower, canola, cottonseed, and other plant-based meals, which themselves may or may not have been subjected to an oil extraction process.

Meat and bone meal is obtained from suppliers such as Darling International, Inc. (Irving, Tex.). Oilseed meal is obtained from suppliers such as Cargill Oilseeds (Cedar Rapids, Iowa). Feather meal is obtained from suppliers such as Agri Trading Corp., (Hutchinson, Minn.). Amino acids are obtained from suppliers such as DuCoa, (Highland, Ill.).

Feed rations are made by mixing various materials such as grains, seed meals, vitamins, and/or purified amino acids together to form a composite material that meets dietary requirements for protein, energy, fat, vitamins, minerals, and other nutrients. The mixing process can include grinding and blending the components to produce a relatively homogeneous mixture of nutrients. Physical properties of the feed raw materials and of the compounded feed affect the nutritional quality, storability, and overall value of the products. Suitable processes for manufacturing feed rations are disclosed in Feed Manufacturing Technology IV (1994, American Feed Industry Association) and incorporated herein in its entirety.

The extracted corn meal may be somewhat analogous to steam-flaked corn in terms of digestibility of the starch fraction, but may have better digestibility in ruminants by virtue of the processing conditions. As discussed herein, specific oil levels can be achieved in the extracted meal by altering processing conditions. The protein, amino acid, and oil levels of the present extracted meal cannot be achieved in steam-flaked normal corn, and steam-flaked high oil corn may have too much oil, which could adversely affect ruminant animal health.

Many types of animal feed rations can be developed using extracted corn meal of the present type, and for illustration purposes, the following diet types will be described herein: (1) meal made from corn grain wherein the said corn grain has an oil content of 12 wt. % and a protein content of 9 wt. %, and meal resulting from this corn has an oil content of 1.5 wt. % for use in a hog finishing diet; and (2) meal made from corn grain wherein the said corn grain has an oil content of 12 wt. % and a protein content of 9 wt. %, and meal resulting from this corn has an oil content of 4.0 wt. % for use in a poultry broiler diet.

Extracted corn meal of the present invention has several advantages over normal corn grain when used as an ingredient in aquaculture feed products. In agriculture, pigments such as carotenoids in feed are often deposited in fatty tissue when consumed resulting in an undesirable color. For some aquaculture species, consumer preference is for very light colored tissue. In other species, such as salmon, consumer preference is for a pink or red tissue. An advantage of extracted corn meal in aquaculture diets is that some undesired pigments will be reduced by virtue of the process to produce extracted corn meal; the solvent-soluble pigment compounds (such as carotenoids) are removed from the meal and concentrated in the oil. A second advantage of extracted corn meal over corn dry-milled or wet-milled corn products is the improved protein content and quality, since the oil has been substantially removed from the kernel resulting in a meal product in which the protein has been concentrated. Because the meal is obtained from all portions of the kernel, including most or all of the embryo, the proteins are generally of higher quality and quantity than would be found in extracted corn grits. By including extracted corn meal in aquaculture feeds, it will be possible to raise animals with fewer undesirable pigment compounds in the tissue.

Solvent extracted corn meal is also useful for fermentation-based production of compounds, such as, for example, ethanol, lactic acid, and vitamins. Solvent extracted corn meal from high oil corn can be hydrolyzed to provide soluble sugars. The meal serves as a carbon and nitrogen source for bacterial, fungal, or yeast cultures. Biotin and other vitamins can be produced through the cultivation of microorganisms. Organisms can include *Pseudomonas mutabilis* (ATCC 31014), *Corynebacterium primorioxydans* (ATCC 31015), Arthrobacter species, Gibberella species, Penicillium species, or combinations thereof.

Nutrients used in the cultivation of these and other microorganisms include, for example, starch, glucose, alcohols, ketones, and as a nitrogen source, peptone, corn steep liquor, soybean powder, ammonium chloride, ammonium sulfate, ammonium nitrate, extracted corn meal, or urea. Various salts and trace elements may also be included in media for the culture of microorganisms. The pH of the culture medium is about 4 to about 9, preferably about 6 to about 8 and most preferably about 7 for bacterial species. The pH is about 5 to about 7 for mold or yeast. During cultivation, temperatures are kept between 10° C. to 100° C., preferably between 20° C. to 80° C., more preferably between about 20° C. to 40° C., and most preferably about 25° C.

Biotin production is described in U.S. Pat. No. 3,859,167, incorporated herein by reference. Cis-tetrahydro-2-oxo-4-n-pentyl-thieno[3,4-d]imidazoline is added to a culture medium containing solvent extracted corn meal and other appropriate identified ingredients in combination with a microbial species capable of forming biotin. In general, the microorganism is cultivated for 1 to 10 days, preferably 1 to 8 days, and more preferably 2 to 7 days, after which time biotin is separated and purified. In one embodiment, to purify biotin, cells are removed from the culture medium, the filtrate is absorbed on activated charcoal, and purified with an ion exchange column. Alternative methods of purification are also used such as crystallization by adjusting the pH of the biotin-contained solution to near its isoelectric point.

Solvent extracted corn meal can also be further processed to produce biodegradable materials. For instance, the meal of the present invention may be incorporated as a thermoplasticising agent. The meal of the invention may be included in the methods described in U.S. Pat. No. 5,320,669, which is incorporated herein by reference. The thermoplastic material is prepared using solvent extracted corn meal, as obtained from the process described herein. In one embodiment, the biodegradable thermoplastic composition prepared using the meal of the present invention is treated with an organic solvent, and optionally a cross-linking agent, to link together the starch and protein of the extracted corn grain. The cross-linking agent referred to herein may be any compound capable of linking the starch and the protein, such as, for example, an aldehyde, an acid anhydride or an epoxide. The compositions so formed using the meal of the present invention can be used to make extruded or molded articles that are biodegradable, water-resistant, and/or have a high level of physical strength.

Blended products comprising the extracted corn meal and one or more other oilseed meals are made by one or more of the following ways: 1) combining the high oil corn and the other oilseed prior to cracking and/or flaking and subjecting the entire seed mixture to the flaking and extraction process described herein to form a blended meal; 2) combining the high oil corn and the other oilseed after cracking and conditioning, but prior to flaking and subjecting the entire seed mixture to an extraction process as described herein to form a blended meal; 3) combining the high oil corn and the other oilseed after flaking and subjecting the entire seed mixture to the extraction process described herein to form a blended meal; 4) combining the extracted corn meal with extracted or non-extracted other oilseed meal to form a blended meal; or 5) combinations thereof to form a blended meal. At any time during these processes, additional components can be added to the blended meals to form a blended product.

The extracted corn meal can also be used in foodstuffs such as snack food, blended food products, breads, fermentation feedstock, breakfast cereals, thickened food products such canned fruit fillings, puffed or extruded foods, and porridge.

When used in edible products for humans or animals, the extracted corn meal can be combined with other components such as other meal, other oilseed meal, grain, other corn, sorghum, wheat, wheat milled byproducts, barley, tapioca, corn gluten meal, corn gluten feed, bakery byproduct, full fat rice bran, and rice hull.

The extracted corn meal can also be used as a raw material for production of corn protein isolates, for fermentation, for further chemical processing, in addition enzymes, such as amylases and proteases, can be added to the meal to help facilitate the breakdown of starch and proteins.

The extracted corn meal is optionally subjected to conventional methods of separating the starch and protein components. Such methods include, for example, dry milling, wet milling, high pressure pumping or cryogenic processes. These and other suitable processes are disclosed in Watson, S. A. & P. E. Ramstad, ed. (1987, Corn: Chemistry and Technology, Ch. 11 and 12, American Association of Cereal Chemist, Inc., St. Paul, Minn.), the disclosure of which is hereby incorporated by reference. Due to the prior removal of oil from the corn meal, the starch and protein components of the extracted corn meal are separated from other components more easily than they would be if the corn oil were not extracted.

Several important quality parameters for the extracted meal include the fat, starch, protein, and moisture content. Methods for evaluating quality parameters of oilseed meals are disclosed in the AOCS methods, the relevant disclosure of which is hereby incorporated by reference. These methods can also be applied to the extracted corn meal prepared as described herein.

The moisture content of the grain can affect the flaking process. It may be necessary for the moisture of the corn grain to be increased by about 1% to about 15% before flaking the seed. Optimizing the grain moisture content to facilitate efficient processing is within the knowledge of those of ordinary skill in the art.

Corn meals derived using different methods or isolated at different times are compared by normalizing the meals to a common moisture content. The moisture content of an oilseed protein concentrate, such as a corn meal or whole corn, is determined using AOCS method Ba 2b-82. The crude fiber content of corn meal is determined using AOCS method Ba 6-84. AOCS method Ba 6-84 is useful for grains, meals, flours, feeds and all fiber bearing material from which the fat can be extracted leaving a workable residue. Crude protein content of corn meal is determined using AOCS method Ba 4e-93. The starch content of corn meal is determined using AOCS method Ba 4e-93. The starch content of corn meal is determined using the Standard Analytical Methods of the Member Companies of the Corn Refiners Association Incorporated, 2d Edition, Apr. 15, 1986, method A-20 ("Corn Refiner's method A-20").

It is to be understood that the analytical methods provided herein are illustrative examples of useful methods for computing various quality parameters for the oils and meals described herein. Other suitable methods are known and may be used to compute the quality parameters disclosed and claimed herein.

The following examples are included to demonstrate specific embodiments of the invention. It should be appreciated by those of skill in the art that the techniques disclosed in the examples which follow represent techniques discovered by the inventors to function well in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Processing High Oil Corn Using Cracking, Conditioning and Flaking Method

This example describes the process of obtaining corn oil and corn meal from high oil corn. A 45-pound sample of high oil corn was cracked using a Roskamp 6.5 Series (9" two sets) set at a roll gap of 0.27 inches. A sample was taken for analysis and the remaining sample split into 4 sub-samples. Each of the four sub-samples was then conditioned independently to different temperatures (120° F., 150° F., 180° F., 200° F.). The samples were heated in a Crown™ 18 inch De-solventiser/Toaster. After each sample reached its conditioning temperature, the samples were passed through flaking rolls. The flaking rolls used were a Ross 10-inch set to a gap of 0.007 inches. A sample of the flakes was taken and about a 500 gram sample was extracted. The flaked sample was washed for four 20-minute periods with 1200 ml of hexanes each period for a total of 4800 ml of solvent over 80 minutes. The solvent temperature was about 120° F. The miscella was collected and filtered through #4 qualitative circles each having a diameter of 185 mm. The filtered miscella was roto-evaporated to estimate the percent oil recovery. The meal was air dried at room temperature. Samples of the oil and meal were taken and analyzed for fatty acid profile, starch, protein and fiber. During the extraction a sieve analysis was performed and flake thickness was measured.

Other equipment used for the analysis included a Mettler Toledo™ HR73 Halogen Moisture Analyzer, Ohaus Explore™ scale, Büchi R-114 Roto-Vap™, Crown™ extractor screen 0.032 sieve and a easy-load master Flex Model 7529-30 pump.

The color of the crude oil was visually evaluated and determined to be a light yellow color compared to crude oil isolated using conventional wet milling methods, which was a dark brown color.

The desolventized corn meal is characterized using AOCS methods Ba 3-38, Ba 2b-82, Ba 6-84, and Ba 4e-93, and Corn Refiner's Method A-20. When normalized to 10% moisture content, the corn meal has about 3.2% by weight fiber content, about 65% by weight starch content, and about 14% by weight protein content. Meal fat is determined to be about 1.07% using AOCS method Ba 3-38. For comparison, corn gluten feed created using conventional wet milling methods and normalized to a 10% moisture content can be expected to contain an oil content of about 4%, a protein content of about 20%, and a fiber and other carbohydrate content of about 60%, all by weight. Also for comparison, corn gluten meal created using conventional wet milling methods and normalized to a 10% moisture content can be expected to contain an oil content of about 3%, a protein content of about 60%, and a fiber and other carbohydrate content of about 22%, all by weight. The nutrient profiles of meal (4.0% by weight oil) produced according to the process of the convention for use in the above blend are shown below. Amounts are expressed on an "as is" or "as fed" moisture level.

The nutrient profiles of two types of meal (1.5 wt. % oil and 4.0 wt. % oil) produced according to this process are shown in Table 8. Amounts are expressed on an "as is" or "as fed" moisture level.

TABLE 8

| Component | Meal Sample 1 Amount (%) | Meal Sample 2 Amount (%) |
| --- | --- | --- |
| Moisture | 12 | 12 |
| Oil | 1.5 | 4 |
| Protein | 10.5 | 10.2 |
| Starch | 58.0 | 56.3 |
| Neutral Detergent Fiber | 11.3 | 11 |
| Acid Detergent Fiber | 2.8 | 2.8 |
| Ash | 1.4 | 1.3 |
| Lysine | 0.39 | 0.37 |
| Tryptophan | 0.105 | 0.102 |
| Methionine | 0.29 | 0.28 |
| Cystine | 0.25 | 0.24 |
| Total Sulfur Amino Acids | 0.54 | 0.52 |
| Valine | 0.53 | 0.51 |
| Isoleucine | 0.40 | 0.39 |
| Arginine | 0.53 | 0.51 |
| Threonine | 0.40 | 0.39 |
| Leucine | 1.20 | 1.17 |
| Histidine | 0.32 | 0.31 |
| Phenylalanine | 0.51 | 0.5 |
| Alanine | 0.82 | 0.79 |
| Serine | 0.54 | 0.52 |

TABLE 8-continued

| Component | Meal Sample 1 Amount (%) | Meal Sample 2 Amount (%) |
| --- | --- | --- |
| True metabolizable energy (TMEn; kcal/kg) | 3023 | 3133 |
| Swine metabolizable energy (ME; kcal/kg) | 3191 | 3301 |

When compared to meals made from conventional corn, the extracted corn meal described herein provides a greater amount of key nutritional components such as vitamins, folic acid, pantothenic acid, lysine, tryptophan, and/or niacin. For example, Meal Samples 1 and 2 of extracted corn meal that are prepared above include the nutritional components in the amounts shown in Table 9. Amounts for the same components, to the extent they are found in yellow corn that has not been processed as described herein, are included for comparison.

TABLE 9

| Component | Yellow Corn | Meal Sample 1 | Meal Sample 2 |
| --- | --- | --- | --- |
| Vitamin B6 (mg/100 g) | 0.400 | 0.820 | 0.660 |
| Vitamin B12 (mg/100 g) | 0.500 | 0.500 | 0.500 |
| Folic Acid (µg/100 g) | — | 25.0 | 25.0 |
| Pantothenic Acid (mg/100 g) | — | 0.660 | 0.890 |
| Niacin (mg/100 g) | 2.05 | 2.30 | 1.15 |

The extracted corn meal prepared as described herein advantageously can be made to contain specific levels of oil and, in particular, specific ratios of oil to protein, of oil to carbohydrate or of oil to protein to carbohydrate. For example, normal corn with 8 wt. % protein and 4 wt. % oil has a protein:oil ratio of 2.0, and high oil corn with 9 wt. % protein and 12 wt. % oil has a protein:oil ratio of 0.75. Meal produced by extraction to have 10.5 wt. % protein and 1.5 wt. % oil has a protein:oil ratio of 7.0. This higher ratio makes this meal type and products made from it desirable for certain applications, one example being a swine-finishing ration.

The present invention provides an extracted corn oil with greater amounts of lutein, zeaxanthin and beta-carotene than commercially available crude oil obtained from commodity normal yellow #2 dent corn. Conventional crude oil can be obtained from suppliers such as Cargill, Incorporated (Minneapolis, Minn.). For example, a corn oil prepared as described above comprised the ingredients shown in Table 10 in the amounts indicated as compared to commercially available crude oil.

TABLE 10

| Sample | Lutein (mg/g) | Zeaxanthin (mg/g) | Beta-Carotene (IU/100 g) |
| --- | --- | --- | --- |
| Commercial Crude Corn Oil | 0.005 | 0.005 | 15.5 |
| Oil Sample 1 | 0.04 | 0.012 | 72.3 |
| Oil Sample 2 | 0.330 | 0.112 | 302 |

EXAMPLE 2

Use of Meal Derived from Corn Processed Through Flaking and Extraction as a Component of Hog Finishing Feed Ration This example details a comparison of two different feed rations: a first feed ration containing normal corn that has not been solvent extracted and a second feed ration containing extracted corn meal. The feed ration containing extracted corn meal is used when lean pork meat is a desired end product. A hog finishing feed ration comprising an extracted corn meal containing less than or about 1.5 wt. % oil is prepared by providing the following ingredients in the amounts indicated in Table 11. The feed ration is generally produced by blending, mixing, and pelletting the ingredients to produce a feed product; however, one or more of these steps can be omitted in the process of preparing the feed ration. Table 11 shows a comparison of swine feed rations made using normal corn (not high oil corn) and extracted corn meal obtained from high oil corn comprising 12 wt. % oil, 9 wt. % protein, wherein the extracted corn meal has about 1.5 wt. % or less of oil (fat). Amounts are expressed on an "as is" or "as fed" moisture level.

TABLE 11

| | Swine Finishing Feed | |
|---|---|---|
| | Normal Corn (%) | Extracted Corn Meal (%) |
| Ingredients | | |
| Corn | 79.98 | — |
| Extracted corn meal (about 1.5% oil) | — | 83.55 |
| Soybean meal | 12.45 | 6.60 |
| Meat & bone meal | 6.59 | 7.22 |
| Feather meal | — | — |
| Fat | 0.10 | 1.50 |
| Salt | 0.40 | 0.70 |
| Lysine | 0.08 | 0.15 |
| Methionine | — | — |
| Premix | 0.15 | 0.15 |
| Nutrient | | |
| Crude protein, % | 15.44 | 15.78 |
| ME, kcal/kg | 3200 | 3200 |
| Crude fiber, % | 1.96 | 2.12 |
| Calcium, % | 0.85 | 0.85 |
| Phosphorus, % | 0.58 | 0.58 |
| Amino Acids, % | | |
| Arginine | 0.96 | 0.93 |
| Cyctine | 0.28 | 0.29 |
| Histidine | 0.40 | 0.42 |
| Isoleucine | 0.57 | 0.58 |
| Leucine | 1.39 | 1.49 |
| Lysine | 0.81 | 0.81 |
| Methionine | 0.26 | 0.34 |
| Phenylalanine | 0.70 | 0.72 |
| Threonine | 0.56 | 0.58 |
| Tryptophan | 0.14 | 0.14 |
| Tyrosine | 0.47 | 0.48 |
| Valine | 0.72 | 0.75 |

In Table 11, absolute values for ingredient percentages are given, however, in practice, the ingredients may include using the inclusion rates shown in other tables herein.

Some advantages of the new feed ration are that a user of the meal would not need to grind the corn, thus saving an energy intensive step, less soybean or other oilseed meal is required to meet desired protein levels, and the meal may have better digestibility than corn grain.

EXAMPLE 3

Use of Meal Derived from Corn Processed through Flaking and Extraction as a Component of Poultry Finishing Feed Ration The feed ration of this example is used to fulfill the high-energy requirements of growing birds such as broilers. A poultry broiler finishing feed ration comprising an extracted corn meal containing less than or about 4 wt. % oil (fat) is prepared by providing the following ingredients in the amounts indicated in Table 12. The feed ration is generally produced by blending, mixing, and pelletting the ingredients to produce a feed product; however, one or more of these steps can be omitted in the process of preparing the feed ration.

Table 12 shows the comparison of poultry feed rations made using normal corn (not high oil corn) and extracted corn meal obtained from high oil corn comprising 12 wt. % oil, 9 wt. % protein, wherein the extracted corn meal has about 4 wt. % or less of oil (fat). Amounts are expressed on an "as is" or "as fed" moisture level and absolute values for ingredient percentages are given, however, in practice, the ingredients may be included using the inclusion rates shown in other tables herein.

TABLE 12

| | Growing Broiler | |
|---|---|---|
| | Normal Corn (%) | Extracted Corn Meal (%) |
| Ingredients | | |
| Normal corn | 66.85 | — |
| Extracted corn meal (about 4% oil) | — | 70.86 |
| Soybean meal | 20.96 | 16.42 |
| Meat & bone meal | 5.00 | 5.00 |
| Feather meal | 2.00 | 2.00 |
| Fat | 3.29 | 3.76 |
| Salt | 0.37 | 0.37 |
| Added Lysine | 0.13 | 0.19 |
| Added Methionine | 0.15 | 0.09 |
| Premix | 0.10 | 0.10 |
| Nutrient | | |
| Crude protein, % | 19.48 | 19.52 |
| ME, kcal/kg | 3100 | 3100 |
| Crude fiber, % | 1.97 | 2.12 |
| Calcium, % | 0.94 | 0.94 |
| Phosphorus, % | 0.63 | 0.62 |
| Amino Acids, % | | |
| Arginine | 1.27 | 1.23 |
| Cyctine | 0.38 | 0.39 |
| Histidine | 0.47 | 0.48 |
| Isoleucine | 0.78 | 0.79 |
| Leucine | 1.68 | 1.74 |
| Lysine | 1.06 | 1.06 |
| Methionine | 0.44 | 0.44 |
| Phenylalanine | 0.92 | 0.92 |
| Threonine | 0.74 | 0.75 |
| Tryptophan | 0.19 | 0.20 |
| Tyrosine | 0.61 | 0.62 |
| Valine | 0.95 | 0.96 |

EXAMPLE 4

Use of Oil Derived from Corn Processed Through Flaking and Extraction as a Component of Food Products, or as a Starting Material for Purification of Kernel Components In this example, oil with approximately a 200% to 300% increase in tocotrienol content over conventionally produced crude corn oil is described. Using the method of flaking and extraction of Example 1, corn oil was extracted from high oil corn grain having an oil content of about 12 wt. %. The corn oil was then analyzed for tocotrienol content. The table below includes data concerning the alpha- and gamma-tocotrienol content of conventional corn oils produced by conventional processing of conventional corn and the extracted corn oil prepared according to the method of Example 1. Conventional Crude oil refers to an unrefined corn oil sample. The sample is representative of corn oil of the type that is most commonly produced presently. As noted below, the tocotrienol content of extracted whole kernel oil (EWKO) samples from two different high oil corn samples that were extracted with solvent at temperatures ranging from 120 to 200° F. was found to be approximately two to three times higher than in the conventional crude oil sample. As shown in Table 13, the tocotrienol content of the EWKO samples ranged from about 26 ppm to about 33 ppm of α-tocotrienol and from about 48 ppm to about 84 ppm of γ-tocotrienol. Generally, increasing the extraction temperature results in an increase in the tocotrienol content of the extracted corn oil. The actual minimum and maximum values for tocotrienol content will depend upon the particular high oil corn used.

TABLE 13

| Sample | α-tocotrienol (ppm) | γ-tocotrienol (ppm) |
| --- | --- | --- |
| Conventional Crude Oil (Control) | 11.88 | 29.94 |
| EWKO 1 (120–200° F.) | 29.36–33.19 | 48.11–59.36 |
| EWKO 2 (120° F.) | 26.05–28.43 | 79.55–84.21 |

EXAMPLE 5

Use of Meal Derived from Corn Processed Through Flaking and Extraction as a Component of a Blended Animal Feed Product Comprised of Corn Meal and an Oilseed Meal This example illustrates a novel feed ingredient comprised of a blend of a corn meal produced by the flaking and oil extraction method and another plant-based meal such as an oilseed meal. This blended material could be in the form of simply a loose aggregate mixture of both meal types or a pelletted product. Because the method for producing the corn and oilseed meals would be similar, i.e., cracking, conditioning, flaking and solvent extraction, it is possible to produce both meals in proximity and blend them prior to shipment to a customer. An advantage of this approach is that varying protein and energy levels can be created in a single meal. Additional ingredients are optionally added either at the meal blending stage or at a later time. For example, an energy-intensive step in feed manufacturing involves grinding corn grain and blending it with other ingredients at a feed mill. The present blended meal generally requires less energy to produce a finished feed product than does a conventional blended meal.

Table 14 shows nutrient profiles of soybean meal (SBM), extracted corn meal (ECM), a blend of 20% SBM and 80% ECM (S20-C80), a blend of 10% SBM and 90% ECM (S10-C90), and nutrient requirements for poultry and swine diets. The poultry and swine nutrient requirements shown are in accordance with National Research Council (NRC) guidelines. The ECM was prepared according to Example 1.

TABLE 14

| Parameter | SBM | ECM | 20% SBM & 80% ECM | Nutrient Needs for Poultry Diets | 10% SBM & 90% ECM | Nutrient Needs for Swine Diets |
| --- | --- | --- | --- | --- | --- | --- |
| Crude Protein (CP) | 47.5 | 10.2 | 17.66 | 18 | 13.93 | 13.2 |
| Swine ME, kcal/kg | 3380 | 3301 | 3316.8 | | 3308.90 | 3265 |
| Poultry ME, kcal/kg | 2440 | 3133 | 2994.4 | 3200 | 3063.70 | |
| Crude Fat, % | 3 | 4 | 3.8 | | 3.90 | |
| Neutral Detergent Fiber, % | 8.9 | 11.3 | 10.82 | | 11.06 | |
| Acid Detergent Fiber, % | 5.4 | 2.8 | 3.32 | | 3.06 | |
| Arginine | 3.48 | 0.45 | 1.06 | 1.00 | 0.75 | 0.19 |
| Histidine | 1.28 | 0.27 | 0.47 | 0.27 | 0.37 | 0.19 |
| Isoleucine | 2.16 | 0.34 | 0.70 | 0.62 | 0.52 | 0.33 |
| Leucine | 3.66 | 1.03 | 1.56 | 0.93 | 1.29 | 0.54 |
| Lysine | 3.02 | 0.33 | 0.87 | 0.85 | 0.60 | 0.60 |
| Methionine | 0.67 | 0.25 | 0.33 | 0.32 | 0.29 | 0.16 |
| Cystine | 0.74 | 0.21 | 0.32 | 0.28 | 0.26 | 0.35 |
| Phenylalanine | 2.39 | 0.44 | 0.83 | 0.56 | 0.64 | 0.34 |
| Tyrosine | 1.82 | 0.29 | 0.60 | 0.48 | 0.44 | 0.55 |
| Threonine | 1.85 | 0.34 | 0.64 | 0.68 | 0.49 | 0.41 |
| Tryptophan | 0.65 | 0.09 | 0.20 | 0.16 | 0.15 | 0.11 |
| Valine | 2.27 | 0.45 | 0.81 | 0.70 | 0.63 | 0.40 |
| Total Essential Amino Acids (EAA) | 23.99 | 4.49 | 8.39 | 6.85 | 6.44 | 4.17 |
| EAA/CP | 0.505 | 0.440 | 0.45 | 0.381 | 0.45 | 0.316 |

EXAMPLE 6

Processing High Oil Corn Using Flaking Method

Shelled kernels of individual ears of yellow dent corn were screened for a total oil content greater than about 7 wt. % oil using a Perten™ bulk near infrared (NIR) seed tester (model 9100-H.F) Perten Instruments (Reno, Nev.). Kernels from the ears having at least a 7 wt. % oil content were screened further for individual kernels having an oil content of at least 13 wt. % oil in a Brimrose™ seedmeister single kernel NIR tester (Brimrose Corp., Baltimore, Md.). The kernels were stored at a moisture content of about 13.5%. At the time of processing, the moisture content of the seed was about 10%.

A bench scale flaking apparatus containing a two-inch stainless steel rod and plate was used to flake the whole corn grain. The whole corn grain sample was passed through the rollers four times to obtain a final flake thickness of about 0.01 inches. A miscella was extracted from the flaked corn grain using hot (60° C. to 65° C.) n-hexane and a Kimble™ model 585050 Soxhlet extractor. The resulting miscella and corn meal were desolventized. The miscella was desolventized by heating the miscella to 70EC under a vacuum of 25 inches of mercury. The corn meal was desolventized according to AOCS method Ba 2a-38.

The total recovered oil was determined to be 14.74 wt. % of the whole corn grain sample. The phosphorus content of the desolventized crude oil was determined to be 365 ppm using AOCS method Ca 12-55. The phospholipid concentration was determined to be 1.095% (0.0365%*30). The free fatty acid content was determined to be 0.2% using AOCS method Ca 5a-40. The neutral oil loss during processing was determined to be 1.3% (1.095%+0.2%). Using the same methods, crude oil extracted from normal, i.e., 3–4 wt. % total oil content, corn grain using conventional wet milling methods can be expected to have a phosphorus content from about 600 ppm to about 800 ppm, a free fatty acid concentration from about 0.5% to about 1.0% and a neutral oil loss during processing ranging from about 3% to about 4%.

The color of the crude oil was visually evaluated and determined to be a light yellow color compared to a crude oil isolated using conventional wet milling methods, which was a dark brown color.

The desolventized corn meal is characterized using AOCS methods Ba 3-38, Ba 2b-82, Ba 6-84, and Ba 4e-93, and Corn Refiner's Method A-20. about 67% starch content, and about 10.15% protein content. Meal fat is determined to be about 6% using AOCS method Ba 3-38. For comparison, corn gluten feed created using conventional wet milling methods and normalized to a 10% moisture content can be expected to contain an oil content of about 4%, a protein content of about 20%, and a fiber and other carbohydrate content of about 60%. Also for comparison, corn gluten meal created using conventional wet milling methods and normalized to a 10% moisture content can be expected to contain an oil content of about 3%, a protein content of about 60%, and a fiber and other carbohydrate content of about 22%.

EXAMPLE 7

Process of Refining High Oil Corn

This example describes a continuous solvent extraction process in the context of the present invention. The extraction process consisted fundamentally of four parts: pre-extraction, extraction, meal desolventization, and oil desolventization. These various stages are described in further detail below.

(A) Pre-extraction 5.4 tons of whole kernel high oil corn (approximately 12 wt. % oil) was tempered and then gate fed from a porta-bin to a bucket elevator to a cracking mill. From the cracking mill, cracks (i.e., particles of whole corn) were conveyed to a conditioner, which discharged to an insulated conveyance system. This system consisted of a second bucket elevator, air mechanical conveyor, heated steam jacketed conveyor, and chutes connected in series. From the conveyance system, corn cracks were fed to a flaking roll.

Prior to transport to the cracking mill, whole corn was tempered to nominally 14.5% moisture by adding water to "as is" moisture corn in a 350 liter Toronto Coppersmithing™ Toreo Model R-12 ribbon blender. Water was sprayed into the vessel at a rate of 2 liters/hr. After the appropriate amount of water was added, the corn was stirred for another hour. The corn was then allowed to soak for 24 hours before being tested for moisture. The tempered corn was then stored for 11 days to 15 days.

After storage, the tempered corn was cracked at ambient temperature using a Roskamp™ (Waterloo, Iowa) model number 6.5 series double stand cracking roll having rolls with 9" diameters and 12" lengths. Both top and bottom rolls were set such that one roll rotated faster than the other. The fast rolls rotated at 1065 revolutions per minute (rpm) with 6 spiral RBV cut corrugations per inch. The slow rolls were cut identically but rotated at 708 rpm. Crack moistures were 13.3% to 15.7%. Cracks of the following average particle size distribution ranges were generated: 15.9% retained by US #4 mesh screens, 39.9% retained by US #6 mesh screens, 27.8% retained by US #8 mesh screens, 6.8% retained by US #10 mesh screens, 4.3% retained by US #18 mesh screens, and 5.3% passed through US #18 mesh screens.

The cracked corn was then conditioned in a two-deck nominal 100-kilogram capacity conditioner (Simon-Rosedowns, currently owned by De Smet; Prins Boudewijnlaan 265; B-2650 EDEGEM; Antwerp) with sweep arm agitation (36 inches in diameter, 20 inches high per deck). The bottom deck was run full. Residence time in the sparged steam section was 55 minutes. The top deck crack depth was varied to achieve a residence time in the indirect heating section averaging 39 minutes and for a total residence time was 94 minutes. Sparge steam addition was a rate from 0 to 5 kg/hr. Conditioning exit moistures were in the range of 12.1% to 14.5%. Exit temperatures were in the range from 75° C. to 85° C.

Flakes were then generated from the cracked corn using a Roskamp (Waterloo, Iowa) model number 2862 flaking mill. The mill was 62 inch long and 28 inch wide rolls. The main drive was designed to turn the fast roll nominally at 300 rpm, and inter-roll drive (IRD) ratio was 8%. Roll pressure was held constant at 500 psig. Flaking exit moistures were in the range of 9.1% to 11.7%. Exit temperatures were in the range from 60° C. to 83° C. Flake thickness ranged from 0.3 mm to 0.7 mm with the roll gap optimally set at 0.2 mm (0.008 inches).

(B) Extraction

A continuous 150 kg/hr Crown™ (Roseville, Minn.) model II pilot extractor was used to process the flaked corn. This pilot scale extractor utilized mixed hexanes as a solvent with 5 counter-current miscella wash zones and a tail wash section. Six-miscella recirculation pumps were utilized with fresh hexanes at 50° C. to 60° C. fed in the upper portion of the extractor. The dimensions of the extractor were 29 feet long, 7.8 inches wide, and 4.5 inches deep. Twenty-three of the 29-foot extractor feet was wetted, of which 19.5 feet was subjected to washing. The average feed rate was approximately 75 kg/hr. The residence time was approximately 60 min. The solvent-to-meal ratios were adjusted between 0.75:1 and 1.33:1. Full miscella was sent to the oil desolventization system at 27° C. to 34° C.

(C) Meal Desolventization

Ambient and indirect heat desolventization occurred first in a Schnecken™ (Crown Iron Works, Roseville, Minn.) steam jacketed conveyor (SJC). The SJC consisted of a hollow flight screw inside of a steam jacket (12 feet long, 10 inches in diameter). The open flight screw created a tumbling action as it conveyed the extracted material through the conveyor, thus ensuring that all material was exposed to the heated wall. A pneumatic controller regulated the amount of steam supplied to the jacket. The temperature at the outlet of the conveyor was monitored and used as the basis for the control of steam supplied to the jacket. Vapors from the conveyor were collected in the low vacuum condenser by the slight negative pressure developed by the system fan. A double-deck nominal 100 kg-capacity desolventizer and toaster (DT) with sweep arm agitation was utilized (36 inches in diameter, 20 inches high per deck). Steam sparge was piped through the top sweep arm only. Meal exit moistures ranged from 9.4% to 17.7%, and exit temperatures ranged from 57° C. to 104° C. Hexanes recovered from the SJC and extractor were condensed, dewatered, and recycled to the extractor.

(D) Oil Desolventization

Oil desolventization was executed using a rising film evaporator (RFE). This unit consisted of sixteen 1.5 cm diameter tubes inside a large jacket. The jacket was filled with steam, heating the tubes. The extract-laden liquid (normally oil in hexanes called miscella) was pumped into the bottom of the tubes. As it traveled up the inside of the tubes, steam heat caused the liquid to boil. The vapors held the liquid against the wall of the tube in a thin, rising film. At the top, the liquid and vapor were allowed to separate. The oil flowed into an overflow pipe to the oil stripper (OS), while the vapors were carried over to a condenser. The tubes were under vacuum so that the liquid boiled at a low temperature.

The oil stripper was a disc and donut style distillation column. The liquid was spread out in a thin film over a disc and dripped down onto a donut back onto a disc allowing the oil to cascade down the column. At the same time, steam was injected into the bottom of the stripper, which passed over the liquid film thereby removing the solvent remaining in the liquid. A steam jacket to keep the liquid and steam hot surrounded the disc and donut column. The oil stripper was also operated under vacuum. Hexanes recovered from the rising film evaporator and the OS were condensed, dewatered, and recycled to the extractor.

(E) Analysis Of Oil Obtained From High Oil Corn

The oil was recovered and analyzed for vitamins, fatty acids, and micronutrients. As a control, 800 lbs. of yellow #2 corn was extracted in an identical manner, and the recovered oil was analyzed for the same components. Vitamin A and β-carotene were analyzed by a contract lab using a proprietary procedure. Alternative published procedures include Bates, et al., *Proc. Fla. State Hort Soc.*, 88, 266–271 (1975). Free fatty acids were analyzed by gas chromatography (GC) using a CP88 cyanopropyl column (100 m×0.265 mm, 0.5 mm film thickness) and a flame ionization detector as described in American Oil Chemist Society (AOCS) methods Ce 1e-91, Ce 2-66, Cd 3 a-94 and Cd 1c-85.

Tocopherols and tocotrienols were analyzed by high performance liquid chromatography (HPLC, Waters model number 2590) using a normal phase silica column with hexane-isopropanol as the mobile phase and detected using fluorescence detection (Waters model number 2690), according to the procedure described in AOCS Ce 8-89. Lutein was analyzed by HPLC using a C30 reverse phase column with water-acetone mobile phase and detected with a UV detector.

Table 15, set forth below, presents a comparison of the oil composition obtained from high oil corn and yellow #2 corn. For comparison, the composition of oil from yellow #2 corn extracted in a corn wet milling process is also given.

TABLE 15

| Component | High Oil Corn | Yellow #2 | Y #2, Corn wet Milling |
|---|---|---|---|
| Palmitic Acid % | 11.4 | 10.7 | 10.7 |
| Stearic Acid % | 2.2 | 1.9 | 2.0 |
| Oleic Acid % | 35.6 | 25.5 | 27.5 |
| Linoleic Acid % | 48 | 58.4 | 57.1 |
| Linolenic Acid % | 0.7 | 1.2 | 1.1 |
| α-Tocotrienol (ppm) | 184 | 48 | 12 |
| α-Tocopherol (ppm) | 237 | 231 | 136 |
| Vitamin B1, mg/100 g | 0.390 | NA | 0.260 |
| Vitamin B2, mg/100 g | 0.090 | NA | 0.080 |
| Vitamin B6, mg/100 g | 0.82 | NA | 0.4 |
| Vitamin B12, mg/100 g | 0.5 | NA | 0.5 |

EXAMPLE 8

Recovering Lighter Particles During Moisture Removal Step

This example sets forth one method of recovering lighter particles, such as fines, generated during the moisture removal step from the processing of high oil corn.

High oil corn is cracked and flaked as described in Example 7. The whole flaked corn from the flaking process is heated to remove moisture using standard processing equipment such as Kice SSI zig-zag classifier model A2612, (Kice Inc., Wichita, Kans.). During the moisture removal step, a controlled air stream is regulated such that the smaller and lighter particles are carried away, hence separating them from the heavier flakes. One such example of the controlled air stream is provided by a Crown™ multi-stage aspirating system operated at 2600 cubic feet-per minute. The lighter particles are recovered by standard process equipment such as a baghouse. The recovered lighter particles are introduced into starch-containing product streams for the recovery of starch.

EXAMPLE 9

Method of Recovering Lighter Particles During Cracking Step With Air

This example sets forth one method of recovering lighter particles such as fines, generated during the cracking step from the processing of high oil corn.

Whole kernels from a high oil corn are cracked using a standard cracking mill roller such as Roskamp 6.5 Series, (Waterloo, Iowa). During this cracking step, a controlled air stream is directed to pass across the cracking mill roller, and the velocity of the air stream is regulated such that the smaller and lighter particles are carried away in the air stream, hence separating them from the heavier particles. One such example of the controlled air stream is provided by a Crown™ multi-stage aspirating system operated at 2600 cubic feet per minute. The lighter particles are recovered by standard process equipment such as a baghouse. The recovered lighter particles are introduced into starch-containing product streams for the recovery of starch.

EXAMPLE 10

Method of Recovering Lighter Particles With Liquid Spray

This example sets forth a method for the recovery of fines generated before and after the flaking process by means of a liquid spray.

High oil corn is processed as described in Example 7. The cracked corn prior to flaking and the corn flakes after the flaking process are sprayed or misted with a source of liquid providing broad enough coverage to physically eliminate the lighter, airborne particles. Water is used as the liquid. Alternatively, the liquid spray can be a substance that adds value to the resulting meal as well as recovers the value from the fines. The liquid spray is typically pure water, process water or water that has been supplemented with nutritional additives such as vitamins, enzymes or minerals. The liquid stream containing the particulates is carried away from the heavier particles in each case and is collected. The particulates are separated from the liquid using standard process equipment including a hydrocyclone or centrifuge. Optionally, the recovered fines may be dried before further use. The recovered lighter particles are then introduced into starch-containing product streams for the recovery of starch.

EXAMPLE 11

Molded Food Product

This example sets forth a description of using the extracted corn meal of the present invention to produce biodegradable materials with improved tensile strength.

Corn meal of the present invention is suspended in hexanes in a sealed container, at a 2:3 corn meal:solvent weight ratio. The mixture is allowed to stand at room temperature without mixing for about 18 hours. The organic solvent is removed from the extracted corn meal, and the extracted corn meal residue is washed during filtering with an aliquot of hexanes in a 1:1 residue:solvent weight ratio. The residue is dried in a convection oven at 50° C. for 16 hours. The dried residue is sprayed with water with mixing until the moisture content of the residue is 10.7% to 11.3%. The solvent-treated extracted corn meal composition is molded into an ASTM standard dogbone article using a compression molding press (Wabash Metal Products, Inc. Wabash, Ind.) at 5000 psi, 140° C. to 160° C. for 10 minutes. The untreated corn meal composition is likewise combined with water to a 10.7% to 11.3% water content and molded into an ASTM standard dogbone article. The articles produced with the solvent-treated extracted corn meal will exhibit significantly improved tensile properties as compared to non-solvent treated extracted corn meal.

Alternatively, corn meal of the present invention is separately suspended in aqueous ethanol (95%) at 1:3 weight-ratio of meal to oil, and boiled for 2 hours with reflux and mechanical stirring. The meal is filtered and the residues are washed with ethanol (1:1 residue:ethanol). The residues are dried, remoistened, and molded according to the procedure above. Tensile properties and water-absorption of the meal treated with ethanol at boiling temperature for a short 2 hour period would be similar to the meals treated at room temperature for an extended 18 hour period.

EXAMPLE 12

Production of Ethanol (A) Starch Hydrolysis

Solvent extracted corn meal of the present invention prepared as described herein is a rich source of starch for fermentation. One method to provide soluble sugars suitable for fermentation is to hydrolyze starch molecules, which are included in the solvent extracted corn meal. About 300 g of corn meal prepared according to the present invention was passed through a 1 mm screen and combined with 700 ml of 99° C. to 100° C. water and 0.5 ml α-amylase in a sealed container. The pH was adjusted to 5.9 with base. The mixture was stirred for 45 minutes and additional α-amylase enzyme was added. After an additional 45 minutes of incubation, the pH of the mixture is adjusted to 4.5 with acid. Half a milliliter (0.5 ml) glucoamylase (Optimax 7525) and 0.5 g protease (Fungal Protease 5000) were added and incubated with both enzymes at 62° C. for 22–24 hours. Throughout the procedure, the degree of starch hydrolysis was monitored by HPLC (Waters 2690 Separations module) using an organic acid column (Aminex HPX-87H Ion Exclusion Column, 300 mm×7.8 mm, Bio Rad).

Total nitrogen content for each sample was determined by Leco 2000 CN. Free amino nitrogen (FAN) was determined by the AOAC method ($15^{th}$ ED. 1990. pg. 735). For comparison, cracked corn grain was prepared and fermented in a manner similar to the extracted corn meal. The amount of dextrose liberated from starch by the milling process and the amount of available nitrogen in the corn samples are outlined in Table 16. YDM displayed the highest dextrose content and HOC the lowest.

Both high oil corn (HOC) and high oil corn meal (HOCM) displayed higher total nitrogen in comparison to yellow dent (YD) and yellow dent meal (YDM). Additionally, HOC and HOCM contained more free amino nitrogen than YD and YDM, respectively. Overall, the milling procedure was fairly consistent for all samples, with weight losses due to evaporation maintained between 4–5%.

TABLE 16

| Corn sample | Dextrose (g/L)* | FAN (ppm) | Total nitrogen (ppm) |
| --- | --- | --- | --- |
| YD | 242.40 | 261.15 | 3437.6 |
| YDM | 311.28 | 195.84 | 4009.6 |
| HOC | 228.02 | 302.95 | 4916.0 |
| HOCM | 240.68 | 232.65 | 5032.0 |

*indicates values obtained after treatment with amylases and protease (B) Fermentation Forty-five grams (45 g) of enzyme-treated corn grits and solvent extracted corn meal (targeting approximately 20% carbohydrate) were added to 125 ml flasks. Yeast extract was added at 1 g/L to ensure that nitrogen was not limiting. Cultures were inoculated with 10% inoculum from overnight yeast cultures (a typical Altech ethanol yeast of *Saccharomyces cerevisiae*) and incubations proceeded for 42 hours at 30° C. on a rotary shaker at 125 rpm. Ethanol production was monitored by HPLC.

Previous studies indicated that yeast grown on YD corn with sugar concentrations near or above 25% did not provide maximal ethanol yields after 42 h. Consequently, media for fermentations were normalized on a weight basis, targeting an initial fermentable sugar concentration of approximately 20%. Starting dextrose concentrations for cultures containing YD, YDM, HOC, and HOCM were 212.21, 236.19, 187.85, and 222.77 g/L, respectively (FIG. 1). Cultures grown on HOC completely utilized the available dextrose, while the other cultures consumed dextrose to less than 1 g/L final concentration. The fastest rate of dextrose consumption was also seen in cultures grown with milled HOC. YD, YDM, and HOCM cultures displayed similar dextrose utilization curves. HOC and HOCM cultures reached over 80 g/L ethanol, but stopped production after 19 hours, possibly due to the limitation of a necessary nutrient. None of the cultures reached the maximum theoretical ethanol yield of 50%, however YD cultures did achieve 45% yield followed by YDM at 43%, HOC at 41% and HOCM at 38% (Table 17). The maximum ethanol yields are relatively close and perhaps minor growth condition adjustments account for the differences.

Examination of ethanol productivity revealed that yeast grown on HOC demonstrated the highest, producing over 5 g/L/h after 7 hours (Table 17). Productivity in these cultures dropped after 19 hours, however by this time all of the dextrose was exhausted. The remaining cultures reached maximum productivity values over 4.5 g/L/h after 19 hours. The ethanol productivity values for the four cultures were quite similar.

TABLE 17

| Fermentation media with: | Ethanol Yield (g EtOH/g sugar) | | | | Ethanol Productivity (g/L/h) | | | |
| --- | --- | --- | --- | --- | --- | --- | --- | --- |
| | 7 h | 19 h | 26 h | 42 h | 7 h | 19 h | 26 h | 42 h |
| YD | 0.10 | 0.40 | 0.45 | 0.41 | 3.51 | 4.92 | 3.97 | 2.26 |
| YDM | 0.12 | 0.38 | 0.43 | 0.40 | 3.65 | 4.6 | 3.81 | 2.21 |
| HOC | 0.19 | 0.41 | 0.39 | 0.39 | 5.14 | 4.11 | 2.91 | 1.76 |
| HOCM | 0.11 | 0.38 | 0.36 | 0.36 | 3.78 | 4.6 | 3.22 | 2.01 |

To ensure that the generation of acidic conditions during fermentation did not influence yeast growth and subsequent ethanol production, the pH of the culture media was monitored (FIG. 2). All cultures dropped in pH, following a similar trend over time and final pH values fell between 3.75 and 3.9. There were no apparent fluctuations in pH to account for differences in ethanol production.

EXAMPLE 13

Aquaculture Feed Comprised of Corn Meal Derived from High Oil Corn

This example sets forth the use of extracted corn meal in an aquaculture feed product.

Two feeding programs are used for two species of fish: tillapia and catfish. One feeding program utilizes a feed including corn grits produced from dry-milled yellow corn grain. The other feeding program utilizes a feed including ECM derived from high oil corn. Feeds are produced with the following ingredients (Table 18):

TABLE 18

| Ingredient | Percent |
| --- | --- |
| Herring Fishmeal | 8 |
| Soybean Meal | 50 |
| Corn | 34.3 |
| Wheat Middlings | 5 |
| Dicalcium Phosphate | 1 |
| Vitamin Mix | 1.5 |
| Trace Mineral Mix | 0.2 |
| Crude Protein (N × 6.25) | 32 |

In the feed ration described in Table 18, extracted corn meal (ECM) can be substituted for some or all of the corn, some or all of the wheat middlings, and/or some of the soybean meal at various levels to produce a desired nutrient profile that can vary depending on the fish species to be fed.

One group of tillapia is fed feed containing extracted corn meal. A second group of tillapia is fed feed containing corn grits. Similarly, one group of catfish is fed feed containing extracted corn meal, and one group of catfish is fed feed-containing corn grits.

The experimental design included four ponds per treatment of one hundred fish per pond, for a total of sixteen ponds and 1,600 fish. Fish within species and ponds are of similar size and weight. Within each species and treatment, fish are fed amounts of feed necessary to support growth rates typical in commercial aquaculture production. Fish are raised from fingerling size to a suitable size reflective of typical market weights, for example, to about one and a half pounds.

Fish are caught and processed in a manner to produce fillets that are compared visually. The effect of extracted corn meal on meat quality is evaluated by measuring the color of the tissue using a color reference guide. A trained and experienced sensory panel is used to evaluate the consumer preference factors such as color and appearance.

The process to produce extracted corn meal separates some of the solvent soluble pigments from the meal portion. Therefore, fish fed with extracted corn meal receive less of these pigments in their diet than fish fed a diet containing corn. Pigments such as carotenoids can be deposited in tissue when consumed in the diet. Therefore, fish fed diets containing extracted corn meal will have lighter colored tissue than fish fed diets containing corn. Growth of fish raised on diets containing extracted corn meal would be similar to fish raised on diets containing corn, but adjustments to the proportions of ration ingredients may need to be made to account for differences in starch digestibility, amino acid availability, and fatty acid content.

EXAMPLE 14

Biodiesel Comprised of Corn Oil Derived from High Oil Corn

This example sets forth the use of oil from high oil corn as a source of an improved biodiesel fuel.

In a continuous process, approximately 62 kg/hr (137 lbs/hr) of oil extracted from high oil corn and refined according to known industry processes, is mixed with 18 kg/hr (40 lbs/hr) of methanol in a stirred tank reaction unit. Simultaneously 0.08 kg/hr (0.1775 lbs/hr) of sodium hydroxide is added to the same stirred tank reaction unit, which operated at 20 psig and approximately 80° C. These conditions provide essentially 100% conversion of added triglycerides to fatty acids and methyl esters.

The two phases of the reaction mixture are allowed to stand and separate to provide methyl esters in the upper phase, and a mixture of glycerol and approximately 10–15 wt. % residual methyl esters, methanol, and base in the lower phase. Approximately 6.4 kg/hr (14 lbs/hr) of the glycerol phase is neutralized, present methanol flashed off, and the remainder is sent to a continuously stirred reaction unit, operated at 80° C. and 320 psig. The reaction unit also contains approximately 4 wt. % Amberlyst-15 catalyst with a residence time of 2 hours and approximately 7.9 kg/hr (17.5 lbs/hr) iso-butylene is fed to the reaction unit. The biodiesel fuel is produced at approximately 66 kg/hr (145 lbs/hr) and has a kinematic viscosity and cloud-point that is greater than biodiesel without glycerol ethers present.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A biodiesel comprising corn oil produced by the extraction of the oil from whole high oil corn.

* * * * *